United States Patent
Burgard

(10) Patent No.: US 6,849,623 B2
(45) Date of Patent: Feb. 1, 2005

(54) XANTHINE AND PHENAZONE-ACESULFAME-H COMPLEXES HAVING IMPROVED TASTE, PROCESS FOR THEIR PREPARATION AND THEIR USE

(75) Inventor: Andreas Burgard, Frankfurt am Main (DE)

(73) Assignee: Nutrinova Nutrition Specialties & Food Ingredients GmbH, Frankfurt am Main (DE)

( * ) Notice: Subject to any disclaimer, the term of this patent is extended or adjusted under 35 U.S.C. 154(b) by 98 days.

(21) Appl. No.: 10/165,399

(22) Filed: Jun. 7, 2002

(65) Prior Publication Data

US 2003/0008865 A1 Jan. 9, 2003

(30) Foreign Application Priority Data

Jun. 25, 2001 (DE) .......................... 101 30 504

(51) Int. Cl.⁷ ...................... A61K 31/54; C07D 291/06
(52) U.S. Cl. .............................. 514/222.5; 544/2; 544/3
(58) Field of Search ....................... 544/3, 2; 514/222.5

(56) References Cited

FOREIGN PATENT DOCUMENTS

| DE | 1 242 622 A | 6/1964 | |
|---|---|---|---|
| DE | 2 000 210 A | 7/1970 | .......... A61K/31/52 |
| DE | 24 53 063 A1 | 5/1976 | .......... C07C/143/86 |
| DE | 198 34 604 A1 | 3/2000 | .......... A61K/31/52 |
| EP | 0 046 506 A1 | 3/1982 | .......... C07D/461/00 |
| EP | 0 155 634 A2 | 9/1985 | .......... C07D/291/06 |
| EP | 0 956 780 A1 | 11/1999 | ............. A23L/2/60 |
| EP | 1 134 223 A2 | 9/2001 | ............. C07F/1/00 |
| IT | 1 242 622 B | 6/1993 | |
| WO | WO 99/04822 A2 | 2/1999 | .......... A61K/47/48 |
| WO | WO 00/07541 A2 | 2/2000 | .......... A61K/31/52 |
| WO | WO 00/12067 A1 | 3/2000 | ............. A61K/9/16 |

OTHER PUBLICATIONS

Von Karl Claub and Harald Jensen, *Angewandte. Chemie*, (1973), 85, 965–973.

Primary Examiner—Richard L. Raymond
(74) Attorney, Agent, or Firm—ProPat, L.L.C.

(57) ABSTRACT

Complex compounds or adducts of xanthine derivatives, for example propentofylline or pentoxyfylline, or phenazone derivatives, for example phenazone, propylphenazone and aminophenazone, and acesulfame-H, in which the components are present in a molar ratio of 1:1 or 1:2, have a pleasantly sweet taste and are suitable for numerous applications, for example in pharmaceuticals. The compounds can be prepared from the dissolved components by simple reaction.

9 Claims, No Drawings

XANTHINE AND PHENAZONE-ACESULFAME-H COMPLEXES HAVING IMPROVED TASTE, PROCESS FOR THEIR PREPARATION AND THEIR USE

BACKGROUND OF THE INVENTION

The present invention relates to xanthine and phenazone-acesulfame-H complexes or adducts having improved taste, process for their preparation, their use and pharmaceuticals comprising such compounds.

Xanthine derivatives, for example propentofylline and pentoxifylline are used as pharmaceuticals in human and veterinary medicine. Corresponding pharmaceuticals are available on the market.

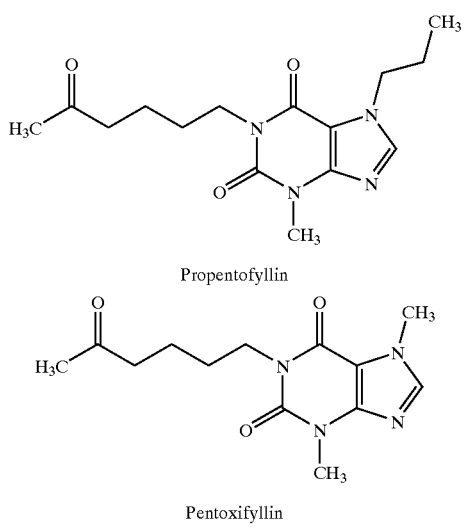

Propentofyllin

Pentoxifyllin

Propentofylline has been used for a number of years in geriatrics in dogs to improve the flow properties of blood in the cerebral and peripheral area. In human medicine, propentofylline is in the advanced stage of clinical development for long-term treatment of patients having Alzheimer's disease and vascular dementia. In clinical studies on humans, propentofylline improved cognitive functions and global functions and activities of everyday life in patients having Alzheimer's disease and vascular dementia.

DE-A 198 34 604 and WO-A 00/07541 also describe the use of propentofylline for treating erectile dysfunctions.

Pentoxifylline has been used for a long time as a pharmaceutical under various trade names, for example Trental®, Azupentat® to improve hemodynamics in human patients suffering from cerebral, peripheral arterial and arteriovenous circulation disorders.

Propentofylline and pentoxifylline and other xanthines and xanthine derivatives, however, have an unpleasantly bitter taste, so that these compounds as active ingredients in pharmaceuticals, because of the unpleasant taste, can cause an aversion in many patients, in particular because these pharmaceuticals have to be taken sometimes for years.

1-Phenyl-2,3-dimethyl-3-pyrazolin-5-one derivatives from the class of substances of phenazones, for example phenazone (Dentigoa® N, Eu-Med mono®) itself, propylphenazone (Arantil P®; R=—CH(CH$_3$)$_2$), aminophenazone (Pyramidon®; R=—N(CH$_3$)$_2$) and metamizole (Novalgin®; R=—NCH$_3$—CH$_2$—SO$_3$Na) have analgesic and antipyretic effects. Phenazones are known active pharmaceutical ingredients and taste very bitter, and masking this unpleasant taste would be desirable, especially if pharmaceuticals which comprise these active ingredients must be taken repeatedly or over a relatively long period.

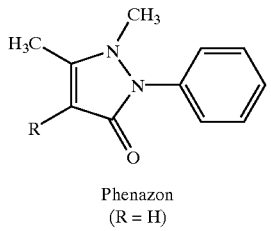

Phenazon
(R = H)

DE-A 1 242 622, EP-A 0 046 506, WO-A 99/04822 and WO-A 00/12067 describe compounds of sweetener and active pharmaceutical ingredients having an improved taste, where in each case the sweetener and the active compound are present in a molar ratio of 1:1. These are acid addition salts or ionic salt compounds in which the sweetener molecule is present as anion. These salts are prepared by an acid-base reaction, the sweetener being reacted as acid with the basic active compound.

It was an object of the present invention to provide xanthine derivatives, for example propentofylline and pentoxifylline, and phenazone derivatives, for example phenazone, in a form which enables their simple use in the preparation of, for example, pharmaceuticals or other preparations, and in which the bitter taste of these active compounds is masked or suppressed. As a result the acceptance of such pharmaceuticals in human and veterinary medicine can be significantly increased and thus the success of therapy, in particular in the case of frequent or long-term intake, can be significantly increased.

BRIEF DESCRIPTIONS OF THE INVENTION

Surprising, it has now been found that xanthine derivatives, for example propentofylline and pentoxifylline (hereinafter called xanthine derivatives; formula II) can react with acesulfame-H(formula I), the acid corresponding to acesulfame-K, to give defined compounds. Acesulfame (6-methyl-3,4-dihydro-1,2,3-oxathiazin-4-one 2,2-dioxide) is, especially in the form of the potassium salt (acesulfame-K), a sweetener available on the market.

DETAILED DESCRIPTION OF THE INVENTION

Not only acesulfame-K, but also acesulfame-H, the acid corresponding to acesulfame-K, can be prepared by known processes (see DE-A 2453 063, Angew. Chemie 85, 965–973 (1973), EP-A 0155 634). In the abovementioned reaction, not only can complexes in general be successfully produced from a xanthine derivative and acesulfame, but also defined compounds from one molecule of xanthine derivative and one or more molecules of acesulfame may also be prepared. The specified molar ratios 1:1 and 1:2 of xanthine derivative to acesulfame have been verified within these defined complexes by means of $^1$H-NMR. Surprisingly, it has been established by x-ray structural analysis that these complexes of xanthine derivative and acesulfame are not salts, which actually would be expected from an acid-base reaction, but are nonionic xanthine derivative-acesulfame adducts which are preferably present in a molar ratio of 1:1 and 1:2. These xanthine derivative-acesulfame adducts are thus not salts, but are characterized by hydrogen bonding between a xanthine derivative molecule and, for example, one or two acesulfame-H molecules. The acesulfame-H, according to x-ray structural analysis, is present in these adducts in its enol form. The reaction diagram below serves to illustrate this fact:

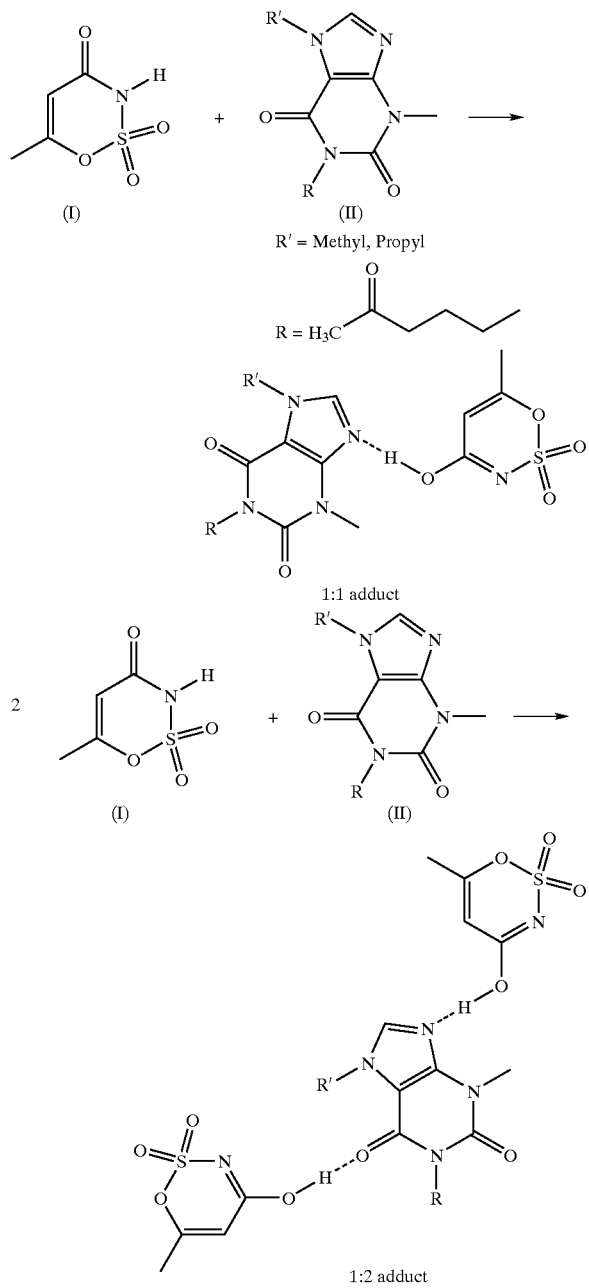

Surprisingly, all of these compounds and their solvates are distinguished by a pleasant sweet taste, with the unpleasant taste component of the xanthine derivative in the 1:1 adduct being significantly decreased compared with the xanthine derivative without acesulfame and in the case of the 1:2 xanthine derivative-acesulfame adduct, being initially completely masked by a citrus-like sweet taste. The following slightly bitter aftertaste of the xanthine derivative is very significantly decreased.

The adduct formation from xanthine derivative and acesulfame, preferably in a defined ratio, leads not only to a reduction or masking of the unpleasant bitter taste of the xanthine derivatives, but the defined 1:1 or 1:2 xanthine derivative-acesulfame adducts can then be incorporated very simply, for example, into chewing gums, chewing tablets or pharmaceuticals without the risk of separation of the starting components. The problem of separation during transport or the metering operation also disappears.

The xanthine derivative-acesulfame adducts are synthesized very simply, for example, from solutions, preferably from aqueous solutions, of the xanthine derivative and of acesulfame-H, in which these substances are preferably present in a molar ratio of 1:1 or 1:2. The resultant reaction solutions are freed from the solvent in a suitable manner, for example in vacuo. In each case the corresponding xanthine derivative-acesulfame adducts result as colorless crystals which, according to $^1$H-NMR spectroscopy, are present in a molar ratio of 1:1 or 1:2 of xanthine derivative-acesulfame. In this manner the corresponding solvates can also be obtained.

The solvent or solvent mixture preferably used is water and/or water-miscible solvent, for example alcohol. The reaction temperatures are preferably from 20 to 100C.

Surprisingly, it has further been found that phenazone (formula II) and phenazone derivatives with acesulfame-H can react to form defined compounds. In this case, for example, preparation of a complex from one molecule of phenazone and one molecule of acesulfame in a molar ratio of 1:1 also succeeds, which has been verified by $^1$H-NMR. These defined complexes are particularly preferred. In addition, the present invention also relates to the corresponding solvates of all complex compounds.

Surprisingly, it has been established by x-ray structural analysis that these complexes of phenazone, or phenazone derivatives, and acesulfame are not salts, which would really be expected from an acid-base reaction, but a nonionic phenazone-acesulfame adduct which is preferably in a molar ratio of 1:1. These phenazone-acesulfame adducts are thus not salts, but preferably form a defined 1:1 adduct via a hydrogen bond between a phenazone molecule and an acesulfame-H molecule. The acesulfame-H, according to x-ray structural analysis, is present in these adducts in its enol form.

The reaction diagram below serves to illustrate this fact:

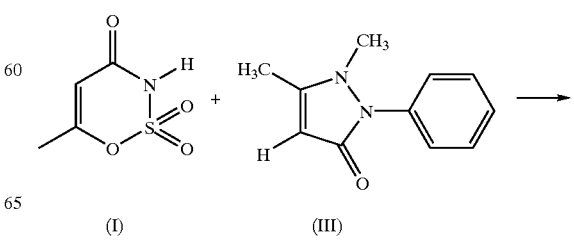

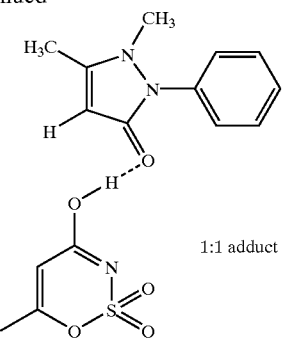

1:1 adduct

Surprisingly, the phenazone-acesulfame adducts and their solvates are distinguished by a pleasant sweet taste, the unpleasant taste component of the phenazone or of its derivatives in the 1:1 adduct being significantly decreased compared with phenazone or its derivative without acesulfame.

Adduct formation from a phenazone derivative and acesulfame in a defined ratio leads not only to a decrease or masking of the unpleasant bitter taste of the phenazone derivatives, but the defined 1:1 adducts can then be very simply incorporated, for example, into chewing gums, chewing tablets or pharmaceuticals without the risk of separation of the starting components. The problem of separation during transport or the metering operation also disappears.

The complexes of phenazone and sweetener or acesulfame and their solvates are prepared in a similar manner to the preparation of the xanthine derivative-acesulfame adducts. In this manner, other phenazone derivatives, for example propylphenazone and aminophenazone or metamizole, can also be reacted with acesulfame-H. The corresponding adducts and their solvates are also the subject matter of the present invention.

The acid sweetener acesulfame-H, in its enol form, thus surprisingly forms defined complexes with heterocyclic compounds which have a carboxamide functionality via a hydrogen bond. This complex formation is here also applicable to other suitable heterocyclic systems which are not yet mentioned, but are also included by the present invention just as is the use of such complexes for preparing preparations, for example in the form of pharmaceuticals, and pharmaceuticals or preparations which comprise such compounds.

The preferred use of the defined inventive complexes and adducts present in a defined molar ratio ensures that the preparations produced therefrom, for example pharmaceuticals, comprise the xanthine derivatives or phenazone derivatives, and the sweetener (acesulfame) in the desired uniform or specified amount. If these components are used or added separately, for example as premix, separations can occur owing to differences in the material properties. That is to say one preparation can comprise, for example, too much sweetener, and another too little sweetener.

Processing the inventive adducts in the pharmaceuticals industry or the food and drink industry, compared with the use of xanthine derivative or phenazone derivative alone, does not require any particular arrangements, but proceeds in accordance with the processes customary there. This also applies to pharmaceutical formulations and their production.

The present invention thus also comprises preparations, preferably pharmaceuticals, for example in the form of tablets or drops, which comprise the inventive complexes or adducts and/or their solvates. In addition, corresponding premixes which comprise these compounds and are used in the production of said preparations, are also subject matter of the invention.

The examples below are intended to describe the invention in more detail.

EXAMPLE 1

Preparation of a 1:1 Adduct from Pentoxifylline and Acesulfame-H 4 mmol (1.113 g) of pentoxifylline together with 4 mmol (0.653 g) of acesulfame-H are dissolved in 20 ml of water at 55° C. The reaction mixture is then concentrated in vacuo. Colorless crystals result with 100% yield which are present as 1:1 adduct, according to $^1$H-NMR.

60-MHz-$^1$H-NMR (DMSO): δ(ppm)=1.6 (m, 4H, CH$_2$-pentoxifylline), 2.2 (s, 3H, CH$_3$-acesulfame), 2.35 (s, 3H, CH$_3$—CO-pentoxifylline), 2.6 (m, 2H, CO—CH$_2$-pentoxifylline), 3.55 (s, 3H, CH$_3$-pentoxifylline), 3,95 (m, 2H, CH$_2$—N-pentoxifylline), (4.05 (s, 3H, CH$_3$-pentoxifylline), 6.3 (s, 1H, CH-acesulfame), 8.25 (s, 1H, CH-pentoxifylline), 11.8 (s, 1H, acesulfame-H)

EXAMPLE 2

Preparation of a 1:2 Adduct from Pentoxifylline and Acesulfame-H 4 mmol (1.113 g) of pentoxifylline together with 8 mmol (1.306 g) of acesulfame-H are dissolved in 20 ml of water at 55° C. The reaction mixture is then concentrated in vacuo. Colorless crystals result at 100% yield, which are present as 1:2 adduct, according to $^1$H-NMR.

60-MHz-$^1$H-NMR (DMSO): δ(ppm)=1.6 (m, 4H, CH$_2$-pentoxifylline), 2.2 (s, 6H, CH$_3$-acesulfame), 2.35 (s, 3H, CH$_3$—CO-pentoxifylline), 2.6 (m, 2H, CO—CH$_2$-pentoxifylline), 3.55 (s, 3H, CH$_3$-pentoxifylline), 3,95 (m, 2H, CH$_2$-N-pentoxifylline), (4.05 (s, 3H, CH$_3$-pentoxifylline), 6.3 (s, 2H, CH-acesulfame), 8.25 (s, 1H, CH-pentoxifylline), 11.8 (s, 2H, acesulfame-H)

EXAMPLE 3

Preparation of a 1:1 Adduct from Phenazone and Acesulfame-H 35 mmol (6.72 g) of phenazone together with 35 mmol (5.71 g) of acesulfame-H are dissolved in 25 ml of methanol at 20° C. The reaction mixture is then concentrated in vacuo. Colorless crystals result at 100% yield which are present as 1:1 adduct according to $^1$H-NMR.

60-MHz-$^1$H-NMR (CDCl$_3$): δ(ppm)=2.1 (s, 3H, CH$_3$-acesulfame), 2.31 (s, 3H, CH$_3$-phenazone), 3.29 (s, 3H, CH$_3$—N-phenazone), 5.6 (s, 1H, CH-acesulfame), 5.7 (s, 1H, CH-phenazone), 8.4 (m, 5H, CH-aromatic), 13.05 (s, 1H, acesulfame-H)

What is claimed is:

1. A compound comprising an adduct formed by a heterocyclic compound having carboxamide functionality and acesulfame-H, and solvates thereof, said acesulfame-H present within said compound as a hydrogen bonded enol moiety.

2. A compound as claimed in claim 1, wherein the heterocyclic compound is a xanthine derivative or phenazone or a phenazone derivative.

3. A compound as claimed in claim 1, wherein it is a compound of propentofylline, pentoxifylline, phenazone, propylphenazone, aminophenazone or metamizole, and acesulfame-H.

4. A compound as claimed in claim 2, wherein the molar ratio of xanthine derivative, phenazone or phenazone derivative to acesulfame-H is 1:1 or 1:2.

5. A compound as claimed in claim 1, wherein it is a nonionic compound.

6. A process for preparing a compound, the compound, comprising an adduct formed by a heterocyclic compound having carboxamide functionality and acesulfame-H, and solvates thereof, the compound formed by reacting the heterocyclic compound and acesulfame-H in the desired molar ratio in a solvent or solvent mixture and optionally subsequently isolating the compound formed, wherein said acesulfame-H is present within said compound as a hydrogen bonded enol moiety.

7. The process as claimed in claim 6, wherein the solvent is water or water-miscible solvent or water and a water miscible solvent.

8. A pharmaceutical composition comprising a compound, said compound comprising an adduct formed by a heterocyclic compound having carboxamide functionality and acesulfame-H, and solvates thereof, said acesulfame-H present within said compound as a hydrogen bonded enol moiety.

9. The preparation as claimed in claim 8, wherein it is a human or veterinary pharmaceutical.

* * * * *